(12) United States Patent
Wright et al.

(10) Patent No.: US 7,926,491 B2
(45) Date of Patent: Apr. 19, 2011

(54) METHOD AND APPARATUS FOR SENSING FIELD STRENGTH SIGNALS TO ESTIMATE LOCATION OF A WIRELESS IMPLANTABLE MARKER

(75) Inventors: J. Nelson Wright, Mercer Island, WA (US); Laurence J. Newell, Mercer Island, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 2224 days.

(21) Appl. No.: 10/382,123

(22) Filed: Mar. 4, 2003

(65) Prior Publication Data

US 2004/0123871 A1 Jul. 1, 2004

Related U.S. Application Data

(60) Provisional application No. 60/437,490, filed on Dec. 31, 2002.

(51) Int. Cl.
*A61B 19/00* (2006.01)
(52) U.S. Cl. .................................................. 128/899
(58) Field of Classification Search .................. 128/897, 128/899; 600/117, 424; 606/130
See application file for complete search history.

(56) References Cited

U.S. PATENT DOCUMENTS

| | | |
|---|---|---|
| 3,349,242 A | 10/1967 | Braestrup |
| 3,577,160 A | 5/1971 | White |
| 3,967,161 A | 6/1976 | Lichtblau |
| 3,969,629 A | 7/1976 | McIntyre |
| 4,023,167 A | 5/1977 | Wahlstrom |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |

(Continued)

FOREIGN PATENT DOCUMENTS

DE 19914455 A1 10/2000

(Continued)

OTHER PUBLICATIONS

International Search Report dated Jan. 24, 2003, PCT Application No. PCT/US02/29390.

(Continued)

*Primary Examiner* — Charles A Marmor, II
*Assistant Examiner* — Christine D Hopkins
(74) *Attorney, Agent, or Firm* — Perkins Coie LLP (57) ABSTRACT

Embodiments of the invention are directed to an apparatus for use in a system that senses an excitable wireless target capable of being implanted in a body or tissue. The apparatus includes multiple electromagnetic field sensors arranged approximately in a common plane, and multiple sense signal output paths coupled to the sensors. Each one of the sensors and corresponding output paths is configured to provide an output signal representing at least a portion of an electromagnetic field provided by the marker, where the output signal is proportional to a component of the field at the sensor, where that component is substantially perpendicular to the plane. Various other configurations regarding this apparatus, as well as the overall system and methods of exciting and receiving signals from wireless markers, are also disclosed.

42 Claims, 5 Drawing Sheets

U.S. PATENT DOCUMENTS

| | | | |
|---|---|---|---|
| 4,633,250 A | 12/1986 | Anderson | |
| 4,642,786 A | 2/1987 | Hansen | |
| 4,643,196 A | 2/1987 | Tanaka et al. | |
| 4,696,287 A | 9/1987 | Hortmann et al. | |
| 4,745,401 A | 5/1988 | Montean | |
| 4,787,098 A | 11/1988 | Silver | |
| 4,795,995 A | 1/1989 | Eccleston | |
| 4,799,495 A | 1/1989 | Hawkins | |
| 4,909,789 A | 3/1990 | Taguchi et al. | |
| 4,936,823 A | 6/1990 | Colvin et al. | |
| 4,994,079 A | 2/1991 | Genese | |
| 5,019,713 A | 5/1991 | Schmidt et al. | |
| 5,031,634 A | 7/1991 | Simon | |
| 5,057,095 A | 10/1991 | Fabian | |
| 5,062,847 A | 11/1991 | Barnes | |
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,170,055 A | 12/1992 | Carroll et al. | |
| 5,189,690 A | 2/1993 | Samuel | |
| 5,216,255 A | 6/1993 | Weidlich | |
| 5,233,990 A | 8/1993 | Barnea | |
| 5,285,772 A | 2/1994 | Rattner et al. | |
| 5,325,873 A | 7/1994 | Hirschi et al. | |
| 5,353,804 A | 10/1994 | Kornberg et al. | |
| 5,377,678 A | 1/1995 | Dumoulin et al. | |
| 5,386,191 A | 1/1995 | McCarten et al. | |
| 5,396,889 A | 3/1995 | Ueda et al. | |
| 5,396,905 A | 3/1995 | Newman et al. | |
| 5,400,787 A | 3/1995 | Marandos | |
| 5,409,004 A | 4/1995 | Sloan | |
| 5,423,334 A | 6/1995 | Jordan | |
| 5,425,367 A | 6/1995 | Shapiro | |
| 5,425,382 A | 6/1995 | Golden et al. | |
| 5,456,718 A | 10/1995 | Szymaitis | |
| 5,509,900 A | 4/1996 | Kirkman | |
| 5,528,651 A | 6/1996 | Leksell | |
| 5,559,435 A | 9/1996 | Harada et al. | |
| 5,621,779 A | 4/1997 | Hughes et al. | |
| 5,638,819 A | 6/1997 | Manwaring et al. | |
| 5,664,582 A | 9/1997 | Szymaitis | |
| 5,680,106 A | 10/1997 | Schrott | |
| 5,697,384 A | 12/1997 | Miyawaki et al. | |
| 5,707,362 A | 1/1998 | Yoon | |
| 5,707,390 A | 1/1998 | Bonutti | |
| 5,727,552 A | 3/1998 | Ryan | |
| 5,731,996 A | 3/1998 | Gilbert | |
| 5,735,795 A | 4/1998 | Young et al. | |
| 5,745,545 A | 4/1998 | Hughes | |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green et al. | |
| 5,951,481 A | 9/1999 | Evans | |
| 5,989,265 A | 11/1999 | Bouquet De La Joliniere et al. | |
| 6,026,818 A | 2/2000 | Blair | |
| 6,059,734 A | 5/2000 | Yoon | |
| 6,061,644 A | 5/2000 | Leis | |
| 6,067,465 A | 5/2000 | Foo | |
| 6,076,008 A | 6/2000 | Bucholz | |
| 6,081,238 A | 6/2000 | Alicot | |
| 6,082,366 A | 7/2000 | Andra et al. | |
| 6,108,400 A | 8/2000 | Siochi | |
| 6,129,668 A | 10/2000 | Haynor et al. | |
| 6,165,135 A | 12/2000 | Neff | |
| 6,198,963 B1 | 3/2001 | Haim et al. | |
| 6,230,038 B1 | 5/2001 | von Gutfeld et al. | |
| 6,246,900 B1 | 6/2001 | Cosman et al. | |
| 6,298,271 B1 * | 10/2001 | Weijand | 607/60 |
| 6,307,473 B1 | 10/2001 | Zampini et al. | |
| 6,363,940 B1 | 4/2002 | Krag | |
| 6,371,379 B1 | 4/2002 | Dames | |
| 6,380,732 B1 | 4/2002 | Gilboa et al. | |
| 6,405,072 B1 | 6/2002 | Cosman | |
| 6,416,520 B1 | 7/2002 | Kynast et al. | |
| 6,474,341 B1 | 11/2002 | Hunter et al. | |
| 6,534,982 B1 | 3/2003 | Jakab | |
| 6,564,807 B1 | 5/2003 | Schulman et al. | |
| 6,611,141 B1 | 8/2003 | Schulz | |
| 6,618,612 B1 * | 9/2003 | Acker et al. | 600/424 |
| 6,675,810 B2 | 1/2004 | Krag | |
| 6,698,433 B2 | 3/2004 | Krag | |
| 6,701,179 B1 | 3/2004 | Martinelli et al. | |
| 6,757,557 B1 * | 6/2004 | Bladen et al. | 600/424 |
| 6,812,842 B2 | 11/2004 | Dimmer | |
| 6,813,337 B2 | 11/2004 | Svatos et al. | |
| 6,822,570 B2 | 11/2004 | Dimmer et al. | |
| 6,838,990 B2 | 1/2005 | Dimmer | |
| 6,905,245 B2 | 6/2005 | Cresens et al. | |
| 6,918,919 B2 | 7/2005 | Krag | |
| 6,965,792 B2 | 11/2005 | Avrin et al. | |
| 6,977,504 B2 | 12/2005 | Wright et al. | |
| 7,026,927 B2 | 4/2006 | Wright et al. | |
| 7,135,978 B2 | 11/2006 | Gisselberg et al. | |
| 2002/0091314 A1 | 7/2002 | Schlossbauer et al. | |
| 2002/0193685 A1 | 12/2002 | Mate et al. | |
| 2003/0041866 A1 | 3/2003 | Linberg et al. | |
| 2003/0066537 A1 | 4/2003 | Fabian et al. | |
| 2003/0088178 A1 | 5/2003 | Owens et al. | |
| 2003/0105394 A1 | 6/2003 | Fabian et al. | |
| 2003/0122653 A1 | 7/2003 | Dimmer | |
| 2003/0149353 A1 | 8/2003 | Boos | |
| 2003/0192557 A1 | 10/2003 | Krag | |
| 2004/0123871 A1 | 7/2004 | Wright et al. | |
| 2004/0125916 A1 | 7/2004 | Herron et al. | |
| 2004/0133101 A1 | 7/2004 | Mate et al. | |
| 2004/0138555 A1 | 7/2004 | Krag et al. | |
| 2004/0158146 A1 | 8/2004 | Mate et al. | |
| 2005/0059884 A1 | 3/2005 | Krag | |
| 2005/0195084 A1 | 9/2005 | Dimmer | |
| 2005/0261570 A1 | 11/2005 | Mate et al. | |

FOREIGN PATENT DOCUMENTS

| | | |
|---|---|---|
| EP | 0531081 A | 3/1993 |
| FR | 2635259 | 2/1990 |
| FR | 2686499 | 7/1993 |
| JP | 8166446 | 6/1996 |
| WO | WO 95/25475 | 9/1995 |
| WO | WO 97/12553 A | 4/1997 |
| WO | WO 98/30166 | 7/1998 |
| WO | WO 98/38908 A | 9/1998 |
| WO | WO 98/40026 | 9/1998 |
| WO | WO 99/30182 | 6/1999 |
| WO | WO 99/33406 | 7/1999 |
| WO | WO 99/40869 | 8/1999 |
| WO | WO 99/58044 | 11/1999 |
| WO | WO 99/58065 | 11/1999 |
| WO | WO 00/38579 | 7/2000 |
| WO | WO 00/51514 | 9/2000 |
| WO | WO 00/53115 | 9/2000 |
| WO | WO 00/65989 | 11/2000 |
| WO | WO 01/34049 | 5/2001 |
| WO | WO 02/39917 | 5/2002 |
| WO | WO 02/39918 | 5/2002 |
| WO | WO 02/100485 | 12/2002 |
| WO | WO 2004/060177 A1 | 7/2004 |
| WO | WO 2004/060475 A2 | 7/2004 |

OTHER PUBLICATIONS

U.S. Appl. No. 10/416,827, filed Nov. 17, 2000, Krag.

U.S. Appl. No. 09/877,498, Mate et al.

U.S. Appl. No. 10/334,700, Herron et al.

European Search Report for Application No. 03814943; Applicant: Calypso Medical Technologies, Inc.; Date of Mailing: Apr. 4, 2008 (2 pages).

International Search Report for Application No. PCT/US03/41140; Applicant Calypso Medical Technologies, Inc.; Date of Mailing: Jun. 1, 2007 (3 pages).

Kirsch S. et al. "Real Time Tracking of Tumor Positions for Precision Irradiation" Cars, Computer Assisted Radiology and Surgery. Proceedings of the International Congress and Exhibition. Proceedings of the International Symposium on Computer Assisted Radiology and Surgery, xx, xx, Jun. 24, 1998, pp. 262-264, XP001061283.

* cited by examiner

Fig. 4

METHOD AND APPARATUS FOR SENSING FIELD STRENGTH SIGNALS TO ESTIMATE LOCATION OF A WIRELESS IMPLANTABLE MARKER

CROSS-REFERENCE TO RELATED APPLICATIONS

This application claims the benefit of U.S. Provisional Application 60/437,490 filed Dec. 31, 2002, which is incorporated by reference herein in its entirety.

TECHNICAL FIELD

Embodiments of the invention relate to systems for sensing miniature markers, such as systems for sensing resonating miniature marker assemblies in tissue for use in healthcare applications.

BACKGROUND

Systems have been developed to activate and detect remote activatable marker assemblies positioned, for example, in or on a selected object or body. The markers generate a signal used to detect the presence of the marker. Many of the activatable markers are hard-wired to a power source or other equipment external from the object. Other systems have been developed that utilize resonating leadless or "wireless" markers. These wireless markers are typically activated or energized by a remote excitation source that wirelessly transmits a strong continuous or pulsed excitation signal. In response to the excitation signal, the wireless markers wirelessly transmit a detectable marker signal that must be distinguished from the strong excitation signal and then analyzed in an effort to try to accurately determine the location of the target. The process of distinguishing a weak marker signal from the strong excitation signal to consistently and accurately determine the location of the marker has proven to be very difficult.

One example is U.S. Pat. No. 5,325,873 to Hirschi et al., which teaches a system that detects the general position of an object within a body of tissue. The detection system includes a three-axis resonant-circuit target attached to the object and a separate hand-held detection probe having a pair of parallel and coaxially aligned transmitter/sensing coils. A current is induced in the transmitter/sensing coils that determines whether a return signal strength of the target is sufficient to be counted as a valid signal. The hand-held detection probe also has a pair of receiver coils positioned within the transmitter coils and connected in a series-opposed fashion. The receiver coils allow for the creation of a null circuit condition when the target is equidistant from each of the receiver coils. The detection probe also has a visual display coupled to the receiver coils and configured to indicate the direction (e.g., left/right/up/down) in which the probe should be moved to center the detection probe over the object for achieving the null circuit condition.

Further details regarding prior systems may be found in U.S. patent application Ser. No. 10/027,675 entitled "System For Excitation Of A Leadless Miniature Marker" filed Dec. 20, 2001, U.S. patent application Ser. No. 10/044,056 entitled "System For Excitation Of A Leadless Miniature Marker" filed Jan. 11, 2002, and U.S. patent application Ser. No. 10/213,980 entitled "System For Spatially Adjustable Excitation Of Leadless Miniature Marker" filed Aug. 7, 2002.

Sizes of various depicted elements are not necessarily drawn to scale, and these various elements may be arbitrarily enlarged to improve legibility. Also, the headings provided herein are for convenience only and do not necessarily affect the scope or meaning of the claimed invention.

DETAILED DESCRIPTION

Embodiments of the invention are directed to an apparatus for use in a system that senses an excitable wireless marker capable of being implanted in a body or tissue. The. apparatus includes multiple electromagnetic field sensors arranged in a locally planar array (e.g., an array in a common plane), and multiple sense signal output paths coupled to the sensors. The sensors and the corresponding output paths are configured to provide an output signal representing at least a portion of an electromagnetic field emitted by the marker; the output signal from a specific sensor is proportional to the component of the field that is substantially perpendicular to the plane of the sensor integrated over its aperture. Various other configurations regarding this apparatus, as well as the overall system and methods of exciting and receiving signals from wireless markers, are also disclosed.

The invention will now be described with respect to various embodiments. The following description provides specific details for a thorough understanding of, and enabling description for, these embodiments of the invention. However, one skilled in the art will understand that the invention may be practiced without these details. In other instances, well-known structures and functions have not been shown or described in detail to avoid unnecessarily obscuring the description of the embodiments of the invention.

Description of Suitable Systems

Figure 1:
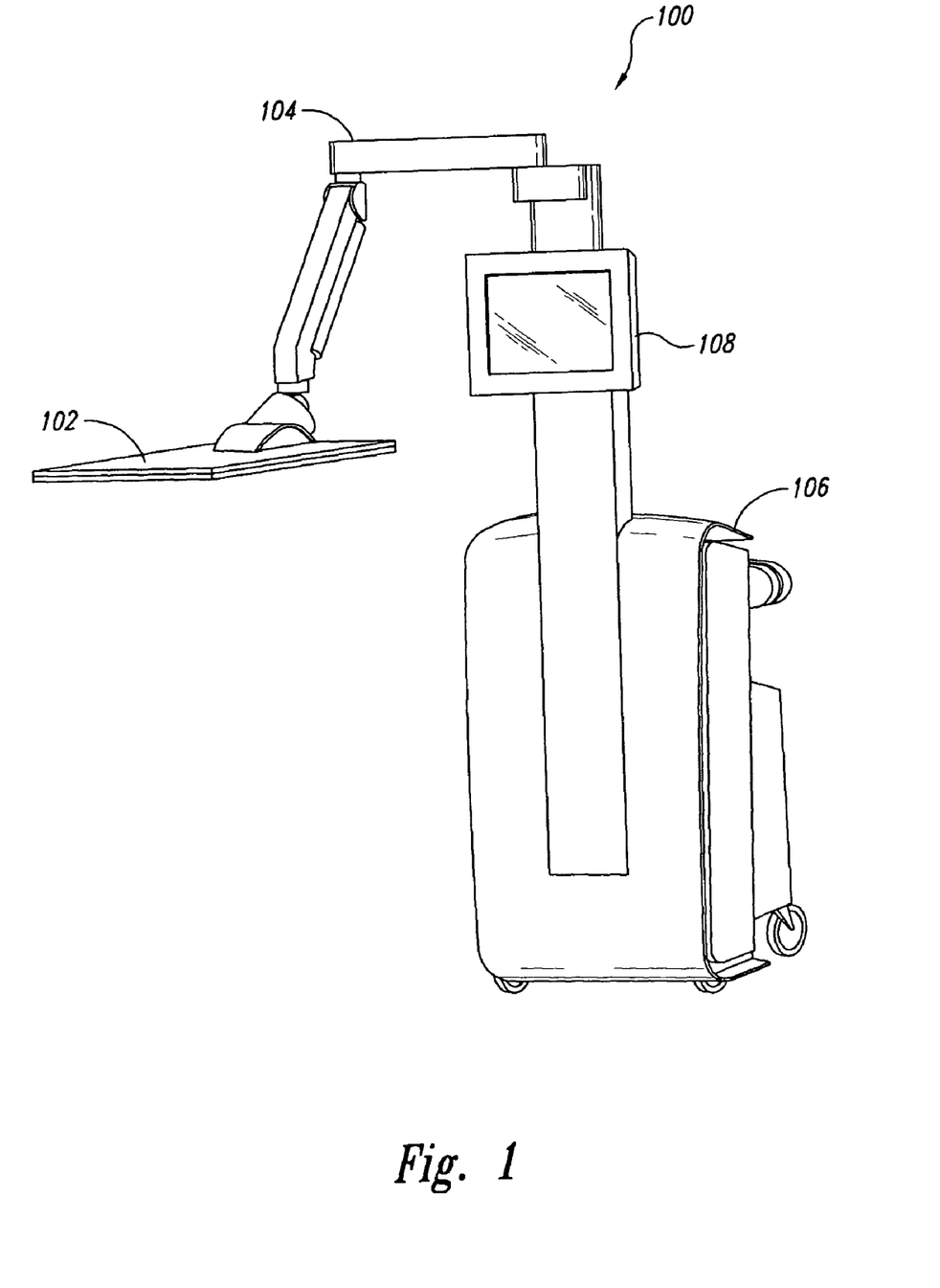
FIG. 1 is a perspective view of an example of a system for estimating the location of wireless implantable markers.

FIG. 1 is a perspective view showing an example of a system 100 for energizing and locating one or more wireless markers in three-dimensional space. The system includes an excitation source and sensor array 102 supported by a movable arm 104. The arm 104 is secured to a base unit 106 that includes various components, such as a power supply, computer (such as an industrial personal computer), and input and output devices, such as a display 108. Many of these components are described in detail below.

The system 100 may be used with guided radiation therapy to accurately locate and track a target in a body to which guided radiation therapy is delivered. Further details on use of the system with such therapy may be found in U.S. patent application Ser. No. 09/877,498, entitled "Guided Radiation Therapy System," filed Jun. 8, 2001, which is herein incorporated by reference.

Figure 2:
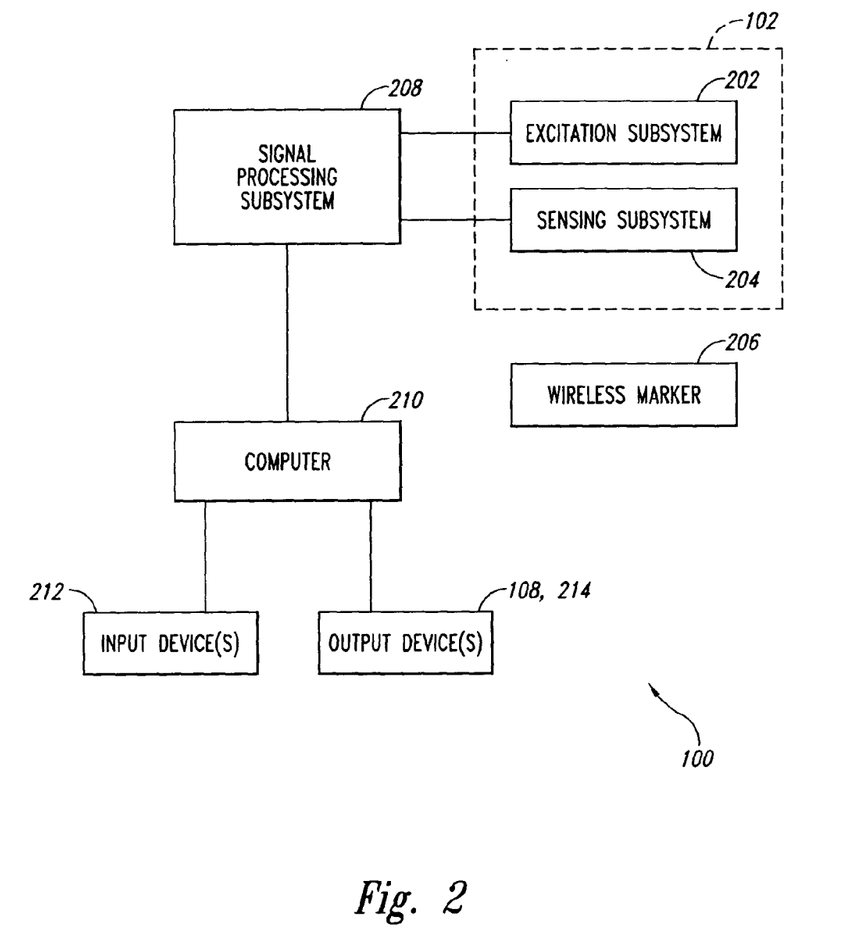
FIG. 2 is a block diagram illustrating components of the system of FIG. 1 including a sensing subsystem.

FIG. 2 is a block diagram of certain components of the system 100. In particular, the excitation source and sensor array 102 includes an excitation subsystem 202 and a sensing subsystem 204. The excitation system 202 outputs electromagnetic energy to excite at least one wireless marker 206, and the sensing system 204 receives electromagnetic energy from the marker. Further details regarding the excitation subsystem 202 may be found in U.S. patent applications noted above. Details regarding the sensing subsystem 204 are provided below.

A signal processing subsystem 208 provides signals to the excitation subsystem 202 to generate the excitation signals. In the embodiment depicted herein, excitation signals in the range of 300 to 500 kilohertz may be used. The signal processing subsystem 208 also receives signals from the sensing subsystem 204. The signal processing subsystem 208 filters, amplifies and correlates the signals received from the sensing subsystem 204 for use in a computer 210.

The computer 210 may be any suitable computer, such as an industrial personal computer suitable for medical applications or environments. One or more input devices 212 are coupled to the computer and receive user input. Examples of such input devices 212 include keyboards, microphones, mice/track balls, joy sticks, etc. The computer generates output signals provided to output devices 214. Examples of such output devices include the display device 108, as well as speakers, printers, and network interfaces or subsystems to connect the computer with other systems or devices.

Unless described otherwise herein, several aspects of the invention may be practiced with conventional systems. Thus, the construction and operation of certain blocks shown in FIG. 2 may be of conventional design, and such blocks need not be described in further detail to make and use the invention because they will be understood by those skilled in the relevant art.

Description of Suitable Sensing Subsystems

Figure 3A:
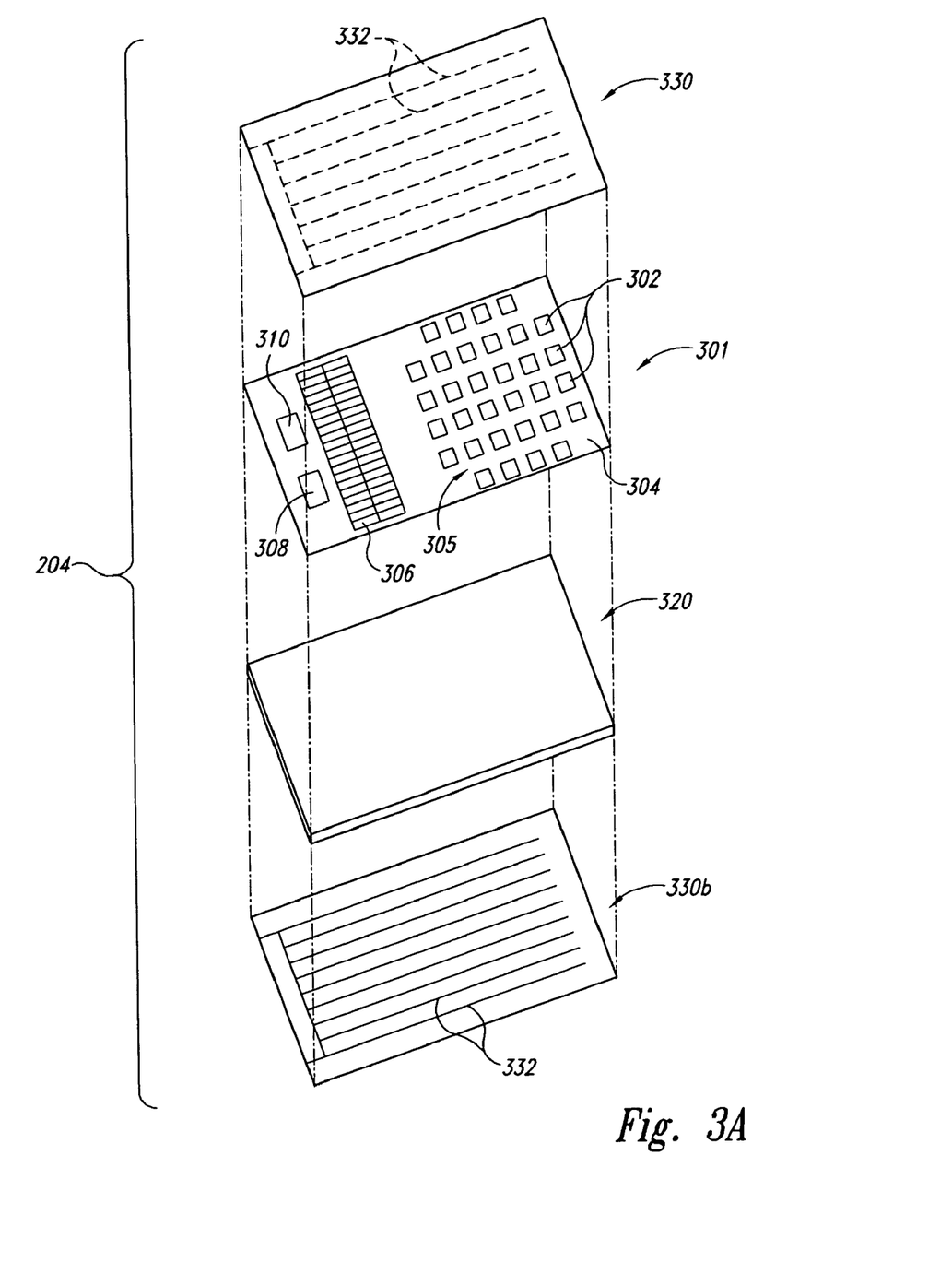
FIG. 3A is an exploded isometric view showing individual components of a sensing subsystem in accordance with an embodiment of the invention.

FIG. 3A is an exploded isometric view showing several components of the sensing subsystem 204. The subsystem 204 includes a sensing assembly 301 having a plurality of coils 302 formed on or carried by a panel 304. The coils 302 can be field sensors or magnetic flux sensors arranged in a sensor array 305. The panel 304 may be a substantially nonconductive sheet, such as KAPTON® produced by DuPont. KAPTON® is particularly useful when an extremely stable, tough, and thin film is required (such as to avoid radiation beam contamination), but the panel 304 may be made from other materials. For example, FR4 (epoxy-glass substrates), GETEK and other Teflon-based substrates, and other commercially available materials can be used for the panel 304. Additionally, although the panel 304 may be a flat, highly planar structure, in other embodiments, the panel may be curved along at least one axis. In either embodiment, the field sensors (e.g., coils) are arranged in a locally planar array in which the plane of one field sensor is at least substantially coplanar with the planes of adjacent field sensors. For example, the angle between the plane defined by one coil relative to the planes defined by adjacent coils can be from approximately 0° to 10°, and more generally is less than 5°. In some circumstances, however, one or more of the coils may be at an angle greater than 10° relative to other coils in the array.

The sensing subsystem 204 shown in FIG. 3A can further include a low-density foam spacer or core 320 laminated to the panel 304. The foam core 320 can be a closed-cell Rohacell foam. The foam core 320 is preferably a stable layer that has a low coefficient of thermal expansion so that the shape of the sensing subsystem 204 and the relative orientation between the coils 302 remains within a defined range over an operating temperature range.

The sensing subsystem 204 can further include a first exterior cover 330a on one side of the sensing subsystem and a second exterior cover 330b on an opposing side. The first and second exterior covers 330a-b can be thin, thermally stable layers, such as Kevlar or Thermount films. Each of the first and second exterior covers 330a-b can include electric shielding 332 to block undesirable external electric fields from reaching the coils 302. The electric shielding, for example, prevents or minimizes the presence of eddy currents caused by the coils 302 or external magnetic fields. The electric shielding can be a plurality of parallel legs of gold-plated, copper strips to define a comb-shaped shield in a configuration commonly called a Faraday shield. It will be appreciated that the shielding can be formed from other materials that are suitable for shielding. The electric shielding can be formed on the first and second exterior covers using printed circuit board manufacturing technology or other techniques.

The panel 304 with the coils 302 is laminated to the foam core 320 using a pressure sensitive adhesive or another type of adhesive. The first and second exterior covers 330a-b are similarly laminated to the assembly of the panel 304 and the foam core 320. The laminated assembly forms a rigid, lightweight structure that fixedly retains the arrangement of the coils 302 in a defined configuration over a large operating temperature range. As such, the sensing subsystem 204 does not substantially deflect across its surface during operation. The sensing subsystem 204, for example, can retain the array of coils 302 in the fixed position with a deflection of no greater than ±0.5 mm, and in some cases no more than ±0.3 mm. The stiffness of the sensing subsystem 204 provides very accurate and repeatable monitoring of the precise location of leadless markers in real time.

The sensing subsystem 204 can also have a low mass per unit area in the plane of the sensor coils 302. The "mass-density" is defined by the mass in a square centimeter column through the thickness of the sensing subsystem 204 orthogonal to the panel 304. In several embodiments, the sensing subsystem 204 has a low-density in the region of the coils 302 to allow at least a portion of the sensing subsystem 204 to dwell in a radiation beam of a linear accelerator used for radiation oncology. For example, the portion of the sensing subsystem 204 including the coils 302 can have a mass density in the range of approximately 1.0 gram/cm$^2$ or less. In general, the portion of the sensing subsystem that is to reside in the beam of a linear accelerator has a mass-density between approximately 0.1 grams/cm$^2$ and 0.5 grams/cm$^2$, and often with an average mass-density of approximately 0.3 grams/cm$^2$. The sensing subsystem 204 can accordingly reside in a radiation beam of a linear accelerator without unduly attenuating or contaminating the beam. In one embodiment, the sensing subsystem 204 is configured to attenuate a radiation beam by approximately only 0.5% or less, and/or increase the skin dose in a patient by approximately 80%. In other embodiments, the panel assembly can increase the skin dose by approximately 50%. Several embodiments of the sensing subsystem 204 can accordingly dwell in a radiation beam of a linear accelerator without unduly affecting the patient or producing large artifacts in x-ray films.

In still another embodiment, the sensing subsystem 204 can further include a plurality of source coils that are a component of the excitation subsystem 202. One suitable array combining the sensing subsystem 204 with source coils is disclosed in U.S. patent application Ser. No. 10/334,700, entitled PANEL-TYPE SENSOR/SOURCE ARRAY ASSEMBLY, filed on Dec. 30, 2002, which is herein incorporated by reference.

Figure 3B:
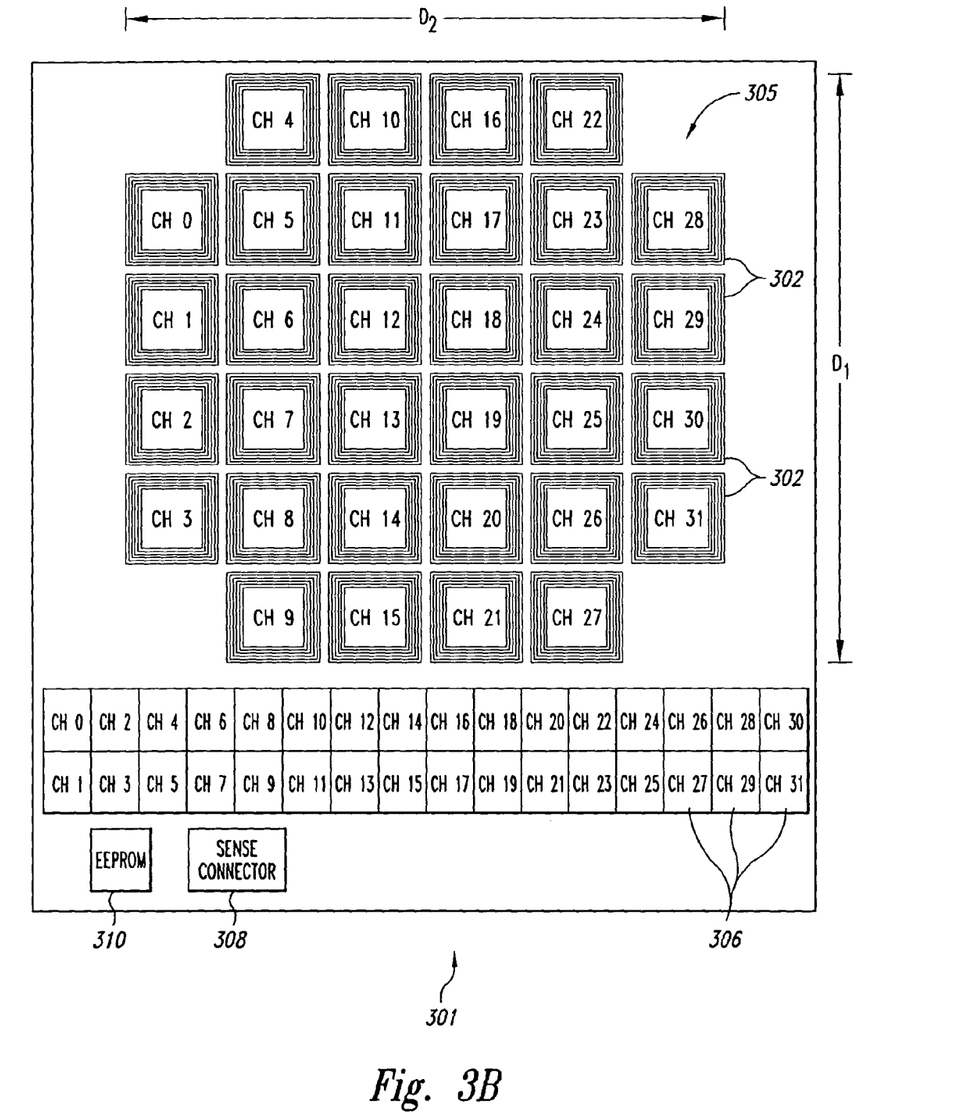
FIG. 3B is a top plan view of an example of a sensing assembly of a sensing subsystem.

FIG. 3B further illustrates an embodiment of the sensing assembly 301. In this embodiment, the sensing assembly 301 includes 32 sense coils 302; each coil 302 is associated with a separate channel 306 (shown individually as channels "Ch 0 through Ch 31"). The overall dimension of the panel 304 can be approximately 40 cm by 54 cm, but the array 305 has a first dimension $D_1$ of approximately 40 cm and a second dimension $D_2$ of approximately 40 cm. The coil array 305 can have other sizes or other configurations (e.g., circular) in alternative embodiments. Additionally, the coil array 305 can have more or fewer coils, such as 8-64 coils; the number of coils may moreover be a power of 2.

The coils 302 may be conductive traces or depositions of copper or another suitably conductive metal formed on the KAPTON® sheet. Each coil 302 has a trace with a width of approximately 0.15 mm and a spacing between adjacent turns within each coil of approximately 0.13 mm. The coils 302 can have approximately 15 to 90 turns, and in specific applications each coil has approximately 40 turns. Coils with less than 15 turns may not be sensitive enough for some applications, and coils with more than 90 turns may lead to excessive voltage from the source signal during excitation and excessive settling times resulting from the coil's lower self-resonant frequency. In other applications, however, the coils 302 can have less than 15 turns or more than 90 turns.

As shown in FIG. 3B, the coils 302 are arranged as square spirals, although other configurations may be employed, such as arrays of circles, interlocking hexagons, triangles, etc. Such square spirals utilize a large percentage of the surface area to improve the signal to noise ratio. Square coils also simplify design layout and modeling of the array compared to circular coils; for example, circular coils could waste surface area for linking magnetic flux from the wireless markers 206. The coils 302 have an inner dimension of approximately 40 mm, and an outer dimension of approximately 62 mm, although other dimensions are possible depending upon applications. Sensitivity may be improved with an inner dimension as close to an outer dimension as possible given manufacturing tolerances. In several embodiments, the coils 32 are identical to each other or at least configured substantially similarly.

The pitch of the coils 302 in the coil array 305 is a function of, at least in part, the minimum distance between the marker and the coil array. In one embodiment, the coils are arranged at a pitch of approximately 67 mm. This specific arrangement is particularly suitable when the wireless markers 206 are positioned approximately 7-27 cm from the sensing subsystem 204. If the wireless markers are closer than 7 cm, then the sensing subsystem may include sense coils arranged at a smaller pitch. In general, a smaller pitch is desirable when wireless markers are to be sensed at a relatively short distance from the array of coils. The pitch of the coils 302, for example, is approximately 50%-200% of the minimum distance between the marker and the array.

In general, the size and configuration of the coil array 305 and the coils 302 in the array 305 depend on the frequency range in which they are to operate, the distance from the wireless markers 206 to the array, the signal strength of the markers, and several other factors. Those skilled in the relevant art will readily recognize that other dimensions and configurations may be employed depending, at least in part, on a desired frequency range and distance from the markers to the coils.

The coil array 305 is sized to provide a large aperture to measure the magnetic field emitted by the markers. It can be particularly challenging to accurately measure the signal emitted by an implantable marker that wirelessly transmits a marker signal in response to a wirelessly transmitted energy source because the marker signal is much smaller than the source signal and other magnetic fields in a room (e.g., magnetic fields from CRTs, etc.). The size of the coil array 305 can be selected to preferentially measure the near field of the marker while mitigating interference from far field sources.

In one embodiment, the coil array 305 is sized to have a maximum dimension $D_1$ or $D_2$ across the surface of the area occupied by the coils that is approximately 100% to 300% of a predetermined maximum sensing distance that the markers are to be spaced from the plane of the coils. Thus, the size of the coil array 305 is determined by identifying the distance that the marker is to be spaced apart from the array to accurately measure the marker signal, and then arrange the coils so that the maximum dimension of the array is approximately 100%-300% of that distance. The maximum dimension of the coil array 305, for example, can be approximately 200% of the sensing distance at which a marker is to be placed from the array 305. In one specific embodiment, the marker 206 has a sensing distance of 20 cm and the maximum dimension of the array of coils 302 is between 20 cm and 60 cm, and more specifically 40 cm.

A coil array with a maximum dimension as set forth above is particularly useful because it inherently provides a filter that mitigates interference from far field sources. As such, one aspect of several embodiments of the invention is to size the array based upon the signal from the marker so that the array preferentially measures near field sources (i.e., the field generated by the marker) and filters interference from far field sources.

For example, consider a circular array of radius r in the plane z=0 with the center of the array at the origin and a marker located over the array at $\{0,0,z_b\}$. Assume the array is comprised of sensors that are (a) responsive to the normal component of an incident field and (b) placed with sufficient density that the sensed signals from a dipolar source can be modeled as spatially continuous across the array. In the limit of $r \to \infty$, the available energy of a dipolar field (i.e., the integral over the plane of the array of the squared normal field) is $$E_\infty = \mu_0^2 m^2 \frac{3(1+\cos^2\phi)}{128\pi z_b^4} \quad (1)$$

where $\mu_0$ is the permeability of free space (or the permeability of the media of interest if a free space model is inappropriate), m is the magnitude of the magnetic moment of the source, and $\phi$ is the angle of the dipole axis from the z axis. The available energy thus drops at 12 dB/octave, i.e., for every doubling of distance, the energy drops by a factor of sixteen. For finite r, let $\xi = z_b/r$, in which case the integrated energy is $$E_r = E_\infty \frac{3(1+4\xi^2+6\xi^4)+(3+12\xi^2+14\xi^4+32\xi^6)\cos^2\phi}{3(1+\xi^2)^4(1+\cos^2\phi)} \quad (2)$$

For small $\xi$, the available energy over a finite array is essentially the same as that over an infinite array, and, as the distance to the source increases, this holds true until $\xi \approx 1$. For sources at greater distances, equation (2) asymptotically approaches −6 dB/octave when $\phi=0$, or −12 dB/octave when $\phi=\pi/2$. Hence an array can be configured to preferentially receive signals from markers which are in its near field (i.e., within approximately 50% of the maximum dimension of the array) compared to sources beyond its near field, which may consist of interfering sources of energy. Specifically, energy from a near field source decreases proportionally to the fourth power of distance from the array, while energy from a far field source decreases asymptotically as the sixth or eighth power of distance from the array.

Thus, when the wireless marker 206 is positioned approximately 20 cm from the sensing subsystem 204, and a radius or maximum dimension of the sensing subsystem is approximately 40 cm, energy from the wireless marker drops off as the fourth power of the distance from the sensing subsystem while environmental noise drops off as the sixth or eighth power of the distance. The environmental noise is thus filtered by the sensing subassembly 204, by virtue of its geometry, to provide better signals to the signal processing subsystem 208.

The size or extent of the array may be limited by several factors. For example, the size of the sensing assembly 301 should not be so large as to mechanically interfere with the movable arm 104 (FIG. 1), the base unit 106 (FIG. 1), or other components, such as a patient couch, rotating gantry of a radiation therapy machine, etc. (not shown in FIG. 1). Also, the size of the array may be limited by manufacturing considerations, such as a size of available panels 304. Further, making a dimension or width of the coil array 305 larger than twice the distance to the wireless marker 206 may yield little performance improvement, but increase manufacturing costs and increase sensitivity to interference.

The coils 302 are electromagnetic field sensors that receive magnetic flux produced by the wireless marker 206 and in turn produce a current signal representing or proportional to an amount or magnitude of a component of the magnetic field through an inner portion or area of each coil. The field component is also perpendicular to the plane of each coil 302. Importantly, each coil represents a separate channel, and thus each coil outputs signals to one of 32 output ports 306. A preamplifier, described below, may be provided at each output port 306. Placing preamplifiers (or impedance buffers) close to the coils minimizes capacitive loading on the coils, as described herein. Although not shown, the sensing assembly 301 also includes conductive traces or conductive paths routing signals from each coil 302 to its corresponding output port 306 to thereby define a separate channel. The ports in turn are coupled to a connector 308 formed on the panel 304 to which an appropriately configured plug and associated cable may be attached.

The sensing assembly 301 may also include an onboard memory or other circuitry, such as shown by electrically erasable programmable read-only memory (EEPROM) 310. The EEPROM 310 may store manufacturing information such as a serial number, revision number, date of manufacture, and the like. The EEPROM 310 may also store per-channel calibration data, as well as a record of run-time. The run-time will give an indication of the total radiation dose to which the array has been exposed, which can alert the system when a replacement sensing subsystem is required.

While shown in only one plane, additional coils or electromagnetic field sensors may be arranged perpendicular to the panel 304 to help determine a three-dimensional location of the wireless markers 206. Adding coils or sensors in other dimensions could increase the total energy received from the wireless markers 206, but the complexity of such an array would increase disproportionately. The inventors have found that three-dimensional coordinates of the wireless markers 206 may be found using the planar array shown in FIG. 3B.

Description of a Suitable Preamplifier

Implementing the sensing subsystem 204 may involve several considerations. First, the coils 302 may not be presented with an ideal open circuit. Instead, they may well be loaded by parasitic capacitance due largely to traces or conductive paths connecting the coils to the preamplifiers, as well as a damping network (described below) and an input impedance of the preamplifiers (although a low input impedance is preferred). These combined loads result in current flow when the coils 302 link with a changing magnetic flux. Any one sense coil 302, then, links magnetic flux not only from the wireless marker 206, but also from all the other sense coils as well. These current flows should be accounted for in downstream signal processing.

A second consideration is the capacitive loading on the coils 302. In general, it is desirable to minimize the capacitive loading on the coils 302. Capacitive loading forms a resonant circuit with the coils themselves, which leads to excessive voltage overshoot when the excitation subsystem 202 is energized. Such a voltage overshoot should be limited or attenuated with a damping or "snubbing" network across the coils 302. A greater capacitive loading requires a lower impedance damping network, which can result in substantial power dissipation and heating in the damping network.

Another consideration is to employ preamplifiers that are low noise. The preamplification can also be radiation tolerant because one application for the sensing subsystem 204 is with radiation therapy systems that use linear accelerators (LINAC). As a result, PNP bipolar transistors and discrete elements may be preferred. Further, a DC coupled circuit may be preferred if good settling times cannot be achieved with an AC circuit or output, particularly if analog to digital converters are unable to handle wide swings in an AC output signal.

Figure 4:
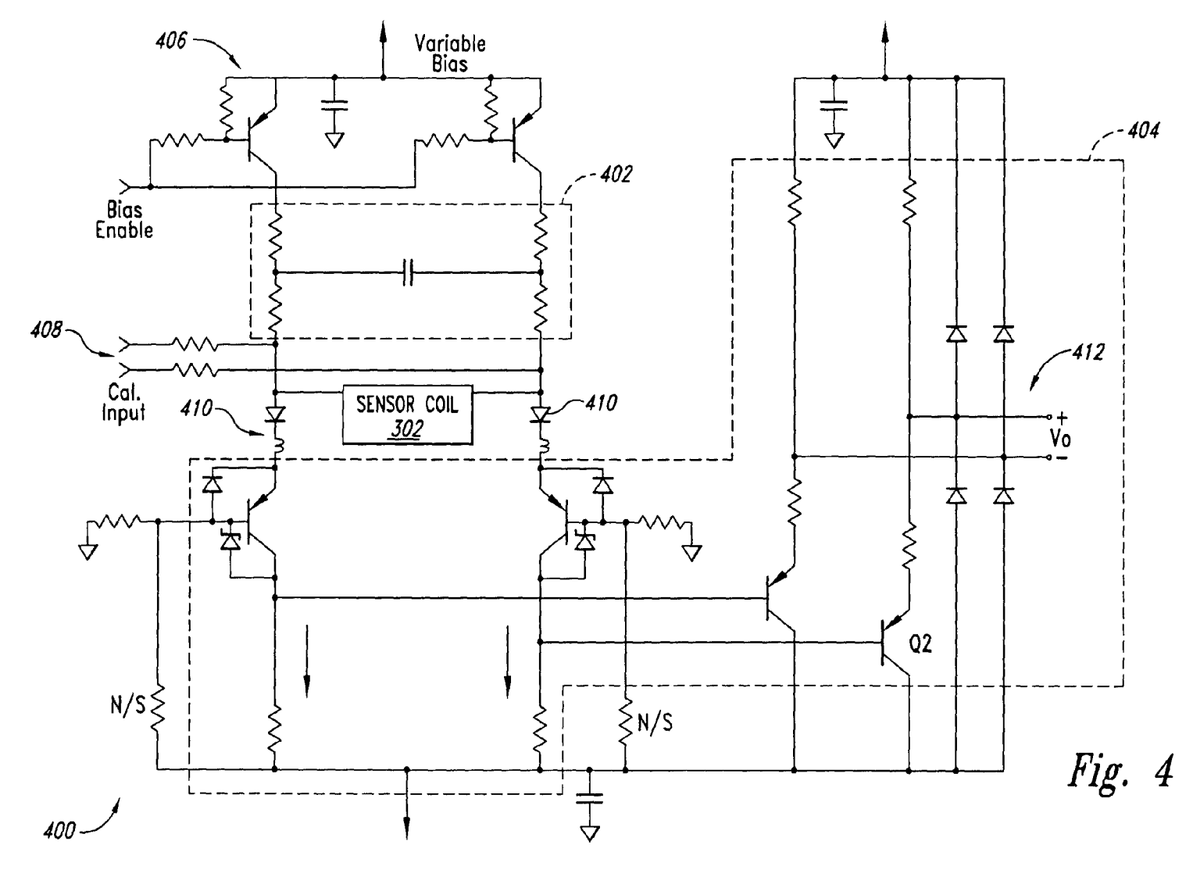
FIG. 4 is a schematic diagram of a suitable preamplifier for use with the sensing subsystem of FIG. 3.

FIG. 4, for example, illustrates an embodiment of a snubbing network 402 having a differential amplifier 404. The snubbing network 402 includes two pairs of series coupled resistors and a capacitor bridging therebetween. A biasing circuit 406 allows for adjustment of the differential amplifier, while a calibration input 408 allows both input legs of the differential amplifier to be balanced. The sensor coil 302 is coupled to an input of the differential amplifier 404, followed by a pair of high voltage protection diodes 410. DC offset may be adjusted by a pair of resistors coupled to bases of the input transistors for the differential amplifier 404 (shown as having a zero value). Additional protection circuitry is provided, such as ESD protection diodes 412 at the output, as well as filtering capacitors (shown as having a 10 nF value).

CONCLUSION

Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to." Words using the singular or plural number also include the plural or singular number, respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, an array of hexagonally shaped sense coils may be formed on a planar array curved along at least one line to form a concave structure. Alternatively, the arrangement of coils on the panel may form patterns besides the "cross" pattern shown in FIGS. 3A and 3B. The coils may be arranged on two or more panels or substrates, rather than the single panel described herein. The teachings of the invention provided herein can be applied to other systems, not necessarily the system employing wireless, implantable resonating targets described in detail herein. These and other changes can be made to the invention in light of the detailed description.

The elements and acts of the various embodiments described above can be combined to provide further embodiments. All of the above U.S. patents and applications and other references are incorporated herein by reference. Aspects of the invention can be modified, if necessary, to employ the systems, functions and concepts of the various references described above to provide yet further embodiments of the invention.

These and other changes can be made to the invention in light of the above detailed description. In general, the terms used in the following claims should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms. For example, while only one aspect of the invention is recited as embodied in a means plus function claim, other aspects may likewise be embodied in a means plus function claim. Accordingly, the inventors reserve the right to add additional claims after filing the application to pursue such additional claim forms for other aspects of the invention.

We claim:

1. In a medical system for sensing an excitable leadless marker capable of being implanted in and/or affixed to a body, an apparatus comprising:
    a rigid support member;
    multiple electromagnetic field sensors arranged in a locally planar array on the support member;
    multiple sense signal output paths carried by the support member, wherein each sense signal output path is coupled to a single one of the electromagnetic field sensors such that each sense signal output path provides an output signal that represents a substantially perpendicular field component from a single one of the field sensors; and
    multiple preamplifiers, wherein each preamplifier is coupled to one of the sense signal output paths, and wherein each preamplifier is a differential amplifier having a high voltage protection snubbing network.

2. The apparatus of claim 1, wherein the support member comprises a flat support panel of a substantially rigid material, and wherein the field sensors are carried by the support panel in a common plane.

3. The apparatus of claim 1, wherein the support member comprises a support panel curved along at least one axis, and wherein the field sensors are carried by the support panel.

4. The apparatus of claim 1, further comprising a flexible sheet, wherein the electromagnetic field sensors and the sense signal paths are conductive depositions on the flexible sheet.

5. The apparatus of claim 1 wherein at least some of the electromagnetic field sensors are arranged as coils having more than 15 windings.

6. The apparatus of claim 1 wherein at least some of the electromagnetic field sensors are arranged as coils having less than 90 windings.

7. The apparatus of claim 1 wherein at least some of the electromagnetic field sensors are arranged as coils.

8. The apparatus of claim 1 wherein at least some of the electromagnetic field sensors are arranged as square spiral coils.

9. The apparatus of claim 1 wherein at least some of the electromagnetic field sensors are arranged as coils having a pitch of approximately 67 millimeters between center points of coils.

10. The apparatus of claim 1 wherein the electromagnetic field sensors include an arrangement of approximately 30 coils of electrically conductive windings.

11. The apparatus of claim 1 wherein the electromagnetic field sensors include an arrangement of coils of electrically conductive traces having a width of approximately 0.15 millimeters.

12. The apparatus of claim 1 wherein the electromagnetic field sensors include an arrangement of coils of electrically conductive traces having a gap width of approximately 0.13 millimeters between adjacent traces in a coil.

13. The apparatus of claim 1 wherein multiple electromagnetic field sensors are configured to receive electromagnetic field signals within a range of 300 to 500 kilohertz.

14. The apparatus of claim 1 wherein the electromagnetic field sensors include an array of coils, wherein each coil receives magnetic flux from the excitable leadless marker and produces a current signal representing an amount of magnetic flux through an inner portion of the coil.

15. The apparatus of claim 1 wherein four electromagnetic field sensors are arranged in an adjacent 2 by 2 array on the support panel.

16. The apparatus of claim 1 wherein the electromagnetic field sensors are arranged in an array having a maximum dimension not greater than approximately 300% of a distance between the array and the leadless marker.

17. The apparatus of claim 1, further comprising at least one electromagnetic field sensor arranged perpendicular to the electromagnetic field sensors arranged in a locally planar array and configured to receive the electromagnetic field emanating from excitation of the leadless marker in a dimension perpendicular to the electromagnetic field sensors arranged in a locally planar array.

18. In a system for energizing a wireless marker to cause the wireless marker to emit a magnetic field signal, and for determining a position of the wireless marker based on the emitted magnetic field signal, wherein the wireless marker is capable of being implanted in and/or affixed to a body, an apparatus for use in the system to receive the emitted magnetic field signal, comprising:
    a support panel having a support sheet, a core, a first outer cover and a second outer cover laminated together;
    an array of at least three locally planar magnetic field sensors at least partially carried by the support panel and configured to sense substantially normal components of the magnetic field signal at different locations on the support panel, and wherein the field sensors comprise spiral traces of a conductive material on the support sheet; and
    three or more active output ports, wherein the active output ports are individually coupled to corresponding magnetic field sensors such that each active output port receives a signal from a single magnetic field sensor and provides an output signal corresponding to one component of the magnetic field signal at the single field sensor.

19. The apparatus of claim 18 wherein the body is organic tissue, and wherein the magnetic field sensors are arranged as approximately planar coils of conductive traces arranged in a substantially rectilinear configuration.

20. In a system for sensing and localizing an excitable wireless marker in or on a human, a sensing system for wirelessly sensing a field emitted by the marker comprising:
  a locally planar support panel comprising a support sheet, a core, a first outer cover and a second outer cover laminated together; and
  a sensor array including at least four field sensors carried by the support panel, the field sensors being at least substantially similar and locally planar relative to each other, wherein the field sensors comprise spiral traces of a conductive material on the support sheet, and wherein each field sensor is responsive only to substantially normal field components relative to the sensors.

21. The sensing system of claim 20 wherein the sensor array comprises 32 field sensors that are coplanar with each other.

22. The sensing system of claim 20 wherein the field sensors comprise rectilinear coils that are coplanar with each other.

23. The sensing system of claim 20 wherein the field sensors are coils arranged in a generally rectilinear pattern.

24. The sensing system of claim 20 wherein the field sensors comprise rectilinear coils having rectilinear spiral traces of an electrically conductive material 25. The sensing system of claim 20 wherein the marker has a predetermined sensing distance at which it is to be positioned apart from the sensing system, and the field sensors occupy an area having a maximum dimension that is approximately 100% to 300% of the predetermined sensing distance.

26. The sensing system of claim 20 wherein the marker has a predetermined sensing distance at which it is to be positioned apart from the sensing system, and the field sensors occupy an area having a maximum dimension that is approximately 200% of the predetermined sensing distance.

27. The sensing system of claim 20 wherein the field sensors are arranged in a symmetrical pattern.

28. The sensing system of claim 20 wherein the field emitted by the marker has a minimum allowable sensing distance, and the field elements are arranged in a pattern having a pitch between 50% to 200% of the minimum allowable sensing distance.

29. In an application for localizing an implantable marker configured to emit a wirelessly transmitted field for measurement from a predetermined sensing distance, a sensing system comprising:
  a support member including a support sheet, a core, a first outer cover and a second outer cover laminated together to form a rigid panel; and
  a plurality of field sensors carried by the support member, the field sensors being at least substantially locally planar relative to one another and responsive to field components normal to individual field sensors, the field sensors including coils having a spiral trace of a conductive material on the support sheet, and the field sensors occupy an area having maximum dimension of approximately 100% to 300% of the predetermined sensing distance.

30. The sensing system of claim 29 wherein the field sensors are coplanar with each other.

31. The sensing system of claim 29 wherein the maximum dimension is approximately 200% of the predetermined sensing distance.

32. The sensing system of claim 29 wherein the field sensors are arranged in a symmetrical pattern.

33. A system for determining a target location in a patient, comprising:
  a marker having a resonating magnetic circuit configured to wirelessly transmit a field in response to a wirelessly transmitted excitation signal; and
  a sensing system comprising (a) a substantially rigid support member including a support sheet, a core, a first outer cover and a second outer cover laminated together and (b) a sensor array including at least four field sensors carried by the support member, and the field sensors being at least a substantially similar and locally planar relative to each other, and wherein the field sensors comprise spiral traces on the support sheet.

34. The system of claim 33 wherein sensor array comprises 32 field sensors that are coplanar with each other.

35. The system of claim 33 wherein the field sensors are rectilinear and coplanar coils.

36. The system of claim 33 wherein the field sensors are coils arranged in a generally rectilinear pattern without a coil in each corner.

37. The system of claim 33 wherein the field sensors comprise rectilinear coils having rectilinear spiral traces of an electrically conductive material.

38. The system of claim 33 wherein the signal transmitted by the marker is to be measured at a predetermined sensing distance and the field sensors occupy an area having a maximum dimension that is approximately 100% to 300% of the predetermined sensing distance.

39. The system of claim 33 wherein the signal transmitted by the marker is to be measured at a predetermined sensing distance and the field sensors occupy an area having a maximum dimension that is approximately 200% of the predetermined sensing distance.

40. The system of claim 33 wherein the sensors are arranged in a symmetrical pattern.

41. The system of claim 33 wherein the signal emitted by the marker has a minimum allowable sensing distance, and the field sensors are arranged in a pattern having a pitch between 50% to 200% of the minimum allowable sensing distance.

42. In a medical system for sensing an excitable leadless marker capable of being implanted in and/or affixed to a body, an apparatus comprising:
  a rigid support member;
  multiple electromagnetic field sensors arranged in a locally planar array on the support member;
  multiple sense signal output paths carried by the support member, wherein each sense signal output path is coupled to a single one of the electromagnetic field sensors such that each sense signal output path provides an output signal that represents a substantially perpendicular field component from a single one of the field sensors;
  at least one electromagnetic field sensor arranged perpendicular to the electromagnetic field sensors arranged in a locally planar array and configured to receive the electromagnetic field emanating from excitation of the leadless marker in a dimension perpendicular to the electromagnetic field sensors arranged in a locally planar array; and
  multiple preamplifiers, wherein each preamplifier is coupled to one of the sense signal output paths, and wherein each preamplifier is a differential amplifier having a high voltage protection snubbing network.

* * * * *